United States Patent [19]

Immel et al.

[11] Patent Number: 5,322,965
[45] Date of Patent: Jun. 21, 1994

[54] PROCESS FOR THE PREPARATION OF A MIXTURE OF CYCLOHEXYLAMINE AND DICYCLOHEXYLAMINE USING A SUPPORTED NOBLE METAL CATALYST

[75] Inventors: Otto Immel; Gerhard Darsow, both of Krefeld; Helmut Waldmann, Leverkusen; Gerd-Michael Petruck, Erkrath, all of Fed. Rep. of Germany

[73] Assignee: Bayer Aktiengesellschaft, Leverkusen, Fed. Rep. of Germany

[21] Appl. No.: 113,581

[22] Filed: Aug. 27, 1993

Related U.S. Application Data

[60] Continuation of Ser. No. 922,258, Jul. 30, 1992, abandoned, which is a division of Ser. No. 840,355, Feb. 24, 1992, abandoned.

[30] Foreign Application Priority Data

Mar. 1, 1991 [DE] Fed. Rep. of Germany ....... 4106543

[51] Int. Cl.$^5$ ............................................ C07C 209/26
[52] U.S. Cl. .................... 564/446; 564/449; 564/450; 564/457; 564/462
[58] Field of Search ............... 564/446, 449, 450, 457, 564/462

[56] References Cited

U.S. PATENT DOCUMENTS

| | | | |
|---|---|---|---|
| 4,487,966 | 12/1984 | Fiedler et al. | 564/446 |
| 4,503,251 | 3/1985 | Gray et al. | 564/449 |
| 4,666,881 | 5/1987 | Wood et al. | 502/325 |
| 4,952,549 | 8/1990 | Immel et al. | 564/462 |

FOREIGN PATENT DOCUMENTS 227868 7/1987 European Pat. Off.

*Primary Examiner*—Glennon H. Hollrah
*Assistant Examiner*—Scott C. Rand
*Attorney, Agent, or Firm*—Sprung Horn Kramer & Woods

[57] ABSTRACT

Optionally substituted cyclohexylamine and optionally substituted dicyclohexylamine can be obtained by catalytic hydrogenation of optionally substituted aniline, a catalyst being employed which contains ruthenium, palladium or a mixture of both metals, which are applied to a support of niobic acid or tantalic acid or a mixture of both. The catalyst contains the noble metal(s) in a total amount from 0.05 to 5% by weight, relative to the total weight of the catalyst. In the case of the use of both noble metals, their weight ratio to one another is 1:9–9:1.

9 Claims, No Drawings

PROCESS FOR THE PREPARATION OF A MIXTURE OF CYCLOHEXYLAMINE AND DICYCLOHEXYLAMINE USING A SUPPORTED NOBLE METAL CATALYST

This application is a continuation of application Ser. No. 922,258, filed Jul. 30, 1992, now abandoned, which is a division of application Ser. No. 840,355, filed Feb. 24, 1992, now abandoned.

BACKGROUND OF THE INVENTION

1. Field of the Invention

The invention relates to a supported catalyst which contains ruthenium, palladium or a mixture of both metals and has a support of niobic acid, tantalic acid or a mixture of both. The invention furthermore relates to a process for the preparation of such a catalyst and to a process for the preparation of a mixture of optionally substituted cyclohexylamine and optionally substituted dicyclohexylamine by catalytic hydrogenation of optionally substituted aniline using the catalyst according to the invention.

2. Description of the Related Art

It is known to prepare cyclohexylamine and other ring-hydrogenated amino compounds by catalytic hydrogenation of aniline and other aromatic amino compounds. Catalysts which are known for this purpose are: cobalt catalysts which contain a basic additive (GB 969,542), Raney-Kobalt (JP 68/03180), ruthenium catalysts (German Auslegeschrift 1,106,319), ruthenium catalysts doped with alkali metal compounds (U.S. Pat. No. 3,636,108) or nickel catalysts (German Patent Specification 805,518).

Most of the processes mentioned are carried out under pressure and give mainly cyclohexylamine apart from only a little dicyclohexylamine. Dicyclohexylamine is therefore frequently prepared by other processes, for example by pressure hydrogenation of diphenylamine using a ruthenium catalyst (German Auslegeschrift 1,106,319). Dicyclohexylamine is additionally formed in the reaction of cyclohexanone with cyclohexylamine in the presence of a palladium/carbon catalyst under a hydrogen pressure of about 4 bar (FR 1,333,692). The process of German Patent Specification 805,518 mentioned is mainly directed to the production of dicyclohexylamine, but is carried out with troublesome returns of by-product.

Other disadvantages of the processes mentioned consist in some cases considerable amounts of cyclohexane waste products, as well as in the unsatisfactory working life of the catalysts employed. There was therefore the desire to develop a process which can be used on an industrial scale, in which the loss due to the formation of cyclohexane is decreased and the working life of the catalyst used is improved, and also to develop a process in which cyclohexylamine and dicyclohexylamine are jointly formed in amounts which are variable according to the demand for the two substances mentioned.

Surprisingly, it has been found that the demands mentioned can be met by the use of the supported noble metal catalyst described in the following.

SUMMARY OF THE INVENTION

The invention accordingly relates to a catalyst containing ruthenium, palladium or a mixture of both on a support containing niobic acid, $Nb_2O_5 \cdot nH_2O$, tantalic acid $Ta_2O_5 \cdot nH_2O$ or a mixture of both, which contains the noble metal(s) in a total amount from 0.05 to 5% by weight, preferably 0.1 to 4% by weight, particularly preferably 0.1 to 3% by weight and in the case of an Ru/Pd mixture contains both metals in a weight ratio of 1:9–9:1, preferably 2:8–8:2, particularly preferably 3:7–7:3, all percentages being based on the total weight of the catalyst.

DETAILED DESCRIPTION OF THE INVENTION

The catalysts according to the invention are accordingly primarily distinguished by the combination of Pd and/or Ru with niobic acid and/or tantalic acid. Compared to the known supported catalysts, such catalysts give higher yields of dicyclohexylamine.

It is particularly a feature of the catalyst according to the invention to employ niobic acid or tantalic acid as the catalyst support or as components of such supports. As is known, niobic acid is a niobium pentoxide hydrate $(Nb_2O_5 \cdot nH_2O)$ which can be obtained, for example, by treatment of aqueous solutions of niobic acid salts with strong mineral acids or by treatment of niobium alkoxides, niobic acid halides or niobic acid esters with water, acids or bases. Niobic acid precipitated in this way is dried and is then a poorly soluble solid compound whose residual water content is not defined, although a niobic acid prepared in this way is superficially a dry powder. The preparation of niobic acid (niobium pentoxide hydrate) is described, for example, in Gmelin's Handbuch der Anorg. Chemie (Gmelin/s Handbook of Inorganic Chemistry), 8th Edition, niobium, part B1, p. 49.

Tantalum pentoxide hydrate (tantalic acid) for the preparation of the catalyst according to the invention can be prepared by hydrolysis of tantalum(V) salts, tantalum(V) alkoxides or other suitable hydrolysable tantalum(V) compounds. The hydrolysis can be performed in a manner analogous to that in the case of the niobium compounds. The carrying-out of such a hydrolysis is fundamentally known to the person skilled in the art, as for Nb, and is described, for example, in Gmelins-Handbuch der Anorg. Chemie (Gmelin's Handbook of Inorganic Chemistry), 8th Edition, tantalum, part B1, (1970), p. 53 and Chem. Lett. 1988, p. 1573. What is written for one of the two elements basically also applies to the other. The great chemical similarity of both elements and their compounds is also expressed in the fact that in their natural occurrence they are largely associated with one another.

Niobic acid is preferentially employed as the support, or as component of such a support, in particular that which contains a content of tantalic acid of natural origin of 0.0001–10 Mol %, relative to the sum of the molar number of niobic and tantalic acid.

In order that the niobic or tantalic acid can be brought into the lump form favourable for use as a solid bed catalyst, the moist precipitate, for example, from the hydrolysis is thoroughly kneaded in a kneader and processed in a granulating apparatus to give moulded articles. The moist moulded articles are then dried, for example, at 120° C. and calcined for 0.5–5 hours at 200°–400° C. A BET surface area of 5–350 cm²/g results in this process. To prepare granules, extrudates or spheres, niobic or tantalic acid can also be compressed with a binder and granulated.

With regard to the catalyst according to the invention, niobic or tantalic acid is an active substance whose activity is also retained by mixing with other solids.

Suitable solids are, for example, titanium dioxide, zinc oxide, magnesium oxide, iron oxide, silicon dioxide, graphite, $Al_2O_3$ and others. These solids can also be employed as binders in the manner described above. Mixtures of niobic or tantalic acid with these inert solids can be employed in a ratio of 5:95–99:1, preferably 50:50–98:2. Preferentially, however, niobic or tantalic acid or a mixture of both is employed on its own as the support. Therewith in an inventive manner, also catalysts are at disposal in which niobic or tantalic acid or a mixture of both constitute only a part of the catalyst support. As such support may be especially mentioned $Al_2O_3$/niobic or tantalic acid-supports, which e.g. can be produced by mixing and compressing the components of such supports or by impregnation and precipitation of niob or tantalum compounds in the form of niobic or tantalic acid on $Al_2O_3 \cdot \gamma\text{-}Al_2O_3$ in the preferred $Al_2O_3$. The contents of niobic and/or tantalic acid may be varied within broad limits, but is preferable of 1–10% by weight based on the support weight.

The invention furthermore relates to a process for the preparation of the catalyst described, which is characterised in that a solution of a salt of ruthenium or palladium or, in the case of the use of both metals, solutions of both salts are impregnated into niobic acid, tantalic acid or a mixture of both, the catalyst is dried after impregnation, and the catalyst is employed in the form then present or after a treatment with hydrogen at 120°–400° C.

The catalyst support is used for the preparation in the form of pills, spheres or fragments of about 1–10 mm. The impregnation of the noble metal salts is carried out in a manner fundamentally known to the person skilled in the art. The drying is performed, for example, at 100°–140° C. and a reduced to normal pressure, for example at 1–1000 mbar, for example in a water pump vacuum.

The noble metal salts can be dissolved in water or in suitable organic solvents. They are preferably dissolved in organic solvents, such as in simple alcohols, ketones, nitriles or cyclic ethers. Examples of such solvents are methanol, ethanol, acetone, acetonitrile and dioxane. Suitable salts of the noble metals are, for example, their chlorides, nitrates or acetates.

After impregnation and subsequent drying, the catalyst according to the invention is fundamentally available. Preferentially, however, it is activated before use by treatment with hydrogen at elevated temperature. Such an elevated temperature is in the range from 120°–400° C., preferably in the range from 150° to 340° C.

The catalysts according to the invention can be employed in an outstanding fashion for the ring hydrogenation of optionally substituted aniline. A mixture of cyclohexylamine and dicyclohexylamine which has the substitution pattern of the aniline employed is formed in this process. Particularly surprisingly, using the catalysts according to the invention the amount of dicyclohexylamine additionally formed compared to monocyclohexylamine can be altered as a function of the hydrogenation temperature, as a result of which controlled preparation of dicyclohexylamine is possible in relatively large amounts.

The invention thus furthermore relates to the use of the inventive catalyst in a process for the preparation of a mixture of optionally substituted cyclohexylamine and optionally substituted dicyclohexylamine by catalytic hydrogenation of optionally substituted aniline on a supported noble metal catalyst, which is characterised in that the catalyst described above is employed and the reaction is carried out at a temperature in the range from 100° to 340° C., preferably 130° to 240° C., and at a pressure of 0.5 to 500 bar, preferably 2 to 400 bar, particularly preferably 100 to 400 bar and very particularly preferably 150 to 350 bar.

This process can therefore be carried out within a wide pressure range, which extends from a pressure close to normal pressure up to a very high pressure. Conceivable embodiments include, for example, working in the gas phase close to normal pressure, working in an autoclave at high pressure and working in the liquid phase, likewise at high pressure.

The hydrogenation of the catalysts according to the invention can therefore be carried out both batchwise and continuously; for industrial purposes, it is preferentially carried out continuously. Advantageously, the process is carried out, as already mentioned, in the liquid phase on a fixed catalyst packing. The catalyst loading in this process is set at an amount from 0.05 to 3 kg, preferably 0.1 to 2 kg, particularly preferably 0.15 to 1.5 kg, of optionally substituted aniline per liter of catalyst and per hour. A slight change in the amount of dicyclohexylamine obtained and also in the yield and selectivity due to the changing activity of the catalyst during the course of relatively long reaction periods can be compensated by a slight adjustment of the reaction temperature or the other parameters. These ratios can be monitored by the analysis of the reaction mixture. Possible starting materials within the meaning of the following reaction equation are aniline and substituted anilines, which are reacted to give the corresponding cyclohexylamines and dicyclohexylamines:

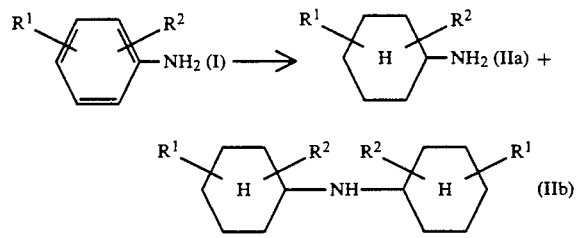

The radicals $R^1$ and $R^2$ independently of one another have the meaning hydrogen, $C_1$-$C_4$-alkyl or $C_1$-$C_4$-alkoxy. Examples of the alkyl and aloxy substituents mentioned are: methyl, ethyl, propyl, isopropyl, butyl, isobutyl, methoxy, ethoxy, propoxy, isopropoxy, butoxy or isobutyoxy. The substituents mentioned preferentially have 1–2 C atoms; they are particularly preferably methyl or methoxy. In a furthermore preferred manner, one of the substituents $R^1$ and $R^2$ has the meaning hydrogen, while the other substituent denotes hydrogen or alkyl or alkoxy in the context mentioned. In a particularly preferred manner, the process according to the invention is directed to the ring hydrogenation of unsubstituted aniline.

According to the invention, substituted aniline is furthermore to be understood as an aniline substituted on the nitrogen by the cyclohexylidene group, which can be prepared in a simple manner by condensation of aniline and cyclohexanone. Such a cyclohexylideneaniline can likewise be ring-substituted and then corresponds to the formula

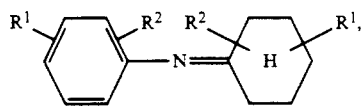

in which $R^1$ and $R^2$ have the scope of meaning given. It is finally furthermore possible to employ such an optionally substituted cyclohexylideneaniline also in the form of a mixture of the optionally substituted cyclohexanone on which it is based with the optionally substituted aniline on which it is based.

Cyclohexylamines and dicyclohexylamines of the scope of meaning mentioned are used for the preparation of antiageing agents for rubbers and plastics, as corrosion inhibitors, and as precursors for plant protection agents and textile auxiliaries.

EXAMPLE 1

75 g of niobic acid, $Nb_2O_5 \cdot nH_2O$, which had been moulded with addition of 3.5% of graphite powder to give 5 mm tablets, were impregnated with a solution which had been prepared from 1.56 g of Pd acetate and 26.8 g of acetonitrile. The niobic acid tablets impregnated in this manner with 1% Pd were dried for 18 hours at 100° C. in a water pump vacuum. The niobic acid was then again impregnated in the same manner with 1% Pd. 60 ml (61 g) of the catalyst prepared were brought into a vertically arranged pressure tube (diameter 14 mm, length 70 cm) which was heated using an oil thermostat. The volume between the particles was filled with fine sea sand (0.2–0.4 mm). The catalyst was first activated with hydrogen for 3 hours at 250° C. and 270 bar, 40 l of hydrogen hourly being released at the lower end of the reaction tube. The hydrogenation of aniline was then started at 270 bar and 182° C., aniline and hydrogen being passed into the catalyst from above. The liquid trickled downwards through the catalyst to a separator. 26 to 62 liters per hour of hydrogen were released at the top of the separator. The amount of aniline continuously fed in corresponded to a catalyst loading in the range from 0.23 to 0.28 g/ml of catalyst/h. Under stationary reaction conditions, the following product composition resulted depending on the hours of operation and the reaction temperatures (the remainder to 100% is by-products).

| Time h | Temperature °C. | DCHA*) % | CHA*) % |
|---|---|---|---|
| 47 | 181 | 82.0 | 17.8 |
| 119 | 171 | 84.5 | 15.3 |
| 263 | 150 | 88.5 | 11.4 |
| 360 | 139 | 91.8 | 8.0 |

*)DHA = dicyclohexylamine;
CHA = cyclohexylamine

EXAMPLE 2

100 g of niobic acid tablets of the same type as in Example 1 were impregnated with a solution which had been prepared from 2.08 g of Pd acetate and 25 g of dioxane. The niobic acid tablets impregnated with 1% Pd were dried for 18 hours at 100° C.

Using 60 ml (59.7 g) of the catalyst prepared, the hydrogenation of aniline was performed in the same manner as in Example 1. The amount of aniline continuously employed corresponded to a catalyst loading of 0.25 g of aniline/ml of cat. × h. Depending on the hours of operation of the catalyst and also the hydrogenation temperature, the following products composition resulted (the remainder to 100% is by-products);

| Time h | Temperature °C. | DCHA*) % | CHA*) % | Aniline % |
|---|---|---|---|---|
| 98 | 179 | 84.2 | 15.6 | — |
| 219 | 179 | 83.8 | 16.0 | 0.05 |
| 411 | 180 | 86.7 | 13.1 | 0.04 |
| 578 | 189 | 85.7 | 13.9 | — |
| 748 | 189 | 86.5 | 13.3 | — |
| 895 | 189 | 86.4 | 13.5 | — |
| 940 | 170 | 92.2 | 7.5 | 0.13 |

*)DCHA - dicyclohexylamine;
CHA - cyclohexylamine

EXAMPLE 3

50 g of niobic acid tablets (d=5 mm) were impregnated with a solution which had been prepared from 3.13 g of $Ru(NO_3)_2$ and 25 g of methanol. The niobic acid impregnated in this way with 2% Ru was dried for 18 hours at 100° C. a water pump vacuum. 25 ml (24 g) of the catalyst thus prepared were used for the hydrogenation of aniline in a 250 ml shaking autoclave which was equipped inside with a sieve basket which was centrally supported and firmly connected to the autoclave and into which the catalyst was poured. Using this catalyst filling, in each case 50 g of aniline were hydrogenated at a hydrogen pressure of 260 to 280 bar at various temperatures. The hydrogenation time was 3 hours in each hydrogenation experiment. Depending on the reaction temperature, the reaction products had the following composition (remainder to 100% is by-products):

| Temperature (°C.) | 110 | 200 |
|---|---|---|
| Aniline | 0.4% | 0.5% |
| Cyclohexylamine | 90.7% | 48.2% |
| Dicyclohexylamine | 8.5% | 50.0% |

Example 4

80 g of $Nb_2O_5 \cdot nH_2O$, which had been tabletted (d=5 mm) with the addition of 1.9% of graphite, were impregnated with a solution which was prepared from 0.83 g of Pd acetate and 17.2 g of acetonitrile. After an intermediate drying—18 hours at 100° C. in the water pump vacuum—the niobic acid tablets were again impregnated with a solution which was prepared from 1.25 g of $Ru(NO_3)_2$ and 17.2 g of methanol. After a fresh drying, the catalyst was ready of use for the hydrogenation. The niobic acid tablets contained 0.5% of Pd and 0.5% of Ru.

25 ml (25.3 g) of the Pd-Ru catalyst thus prepared were used for the hydrogenation of aniline in a 0.25 l shaking autoclave. The autoclave was equipped inside with a sieve basket into which the catalyst was poured. Using this catalyst filling, 50 g of aniline were hydrogenated twice in succession at a hydrogen pressure of 260–280 bar and at various temperatures. After the individual hydrogenations, the autoclave was cooled to room temperature, the reaction product was removed and the autoclave was again charged with aniline. In this case, depending on the temperature, the following product composition resulted at a constant hydrogenation time of 3 hours (remainder to 100% is by-products):

| Temperature (°C.) | 180 | 200 |
|---|---|---|
| Aniline | 0.1% | 0.5% |
| Cyclohexylamine | 69.8% | 38.5% |
| Dicyclohexylamine | 29.4% | 56.3% |

Example 5

15 ml (15.5 g) of the catalyst prepared analogously to Example 1 were employed for the hydrogenation of aniline in the gas phase. The catalyst was first activated for one hour in a stream of hydrogen of 20 l/h at 190° C. 1.54 g of aniline together with 20 l of hydrogen were passed per hour through the activated catalyst, which was situated in a vertically arranged 17 mm wide reaction tube. The resulting reaction product was condensed and analyzed after various time intervals. In this case, depending on the hours of operation of the catalyst, the following composition of the reaction products was found (remainder to 100% is by-products):

| Duration of experiment | 116 h | 238 h | 303 h | 438 h |
|---|---|---|---|---|
| Cyclohexylamine | 22.5 | 22.1 | 18.8 | 18.5 |
| Dicyclohexylamine | 74.2 | 74.6 | 77.9 | 77.9 |
| N-Cyclohexylaniline | 1.2 | 1.2 | 1.2 | 1.4 |
| Aniline | 0.4 | 0.6 | 1.2 | 0.7 |

Example 6

25 ml (24.8 g) of the catalyst prepared according to Example 2 were used for the hydrogenation of cyclohexylideneaniline in a 250 ml shaking autoclave which was equipped inside with a sieve basket which was centrally supported and firmly connected to the autoclave, and into which the catalyst was poured. Using this catalyst filling, 50 g of cyclohexylideneaniline in each case were hydrogenated at various temperatures at a hydrogen pressure of 280 bar. About 95% of cyclohexylideneaniline was contained in the starting product. The hydrogenation time was 3 hours in all experiments of this series. The hydrogenation products had the following composition (remainder to 100% are by-products):

| Temperature (°C.) | 200 | 100 |
|---|---|---|
| Dicyclohexylamine % | 89.1 | 89.9 |
| Cyclohexylamine % | 0.9 | 1.25 |
| N-Cyclohexylaniline | — | 3.5 |

Example 7

Reusing the apparatus described in Example 1 together with catalyst filling (2% Pd on $Nb_2O_5 \cdot nH_2O$), a mixture of cyclohexanone and aniline in a molar ratio of 0.9:1 was employed instead of aniline. The amount of starting material continuously fed in corresponded to a catalyst loading of 0.26 g of mixture/ml of catalyst/h. About 50 liters of hydrogen per hour were released at the top of the separator. Under stationary reaction conditions, the following product composition resulted depending on the reaction temperature (the remainder to 100% is by-products).

| Temperature Running time | 180° C. (φ from) 47 h | 141° C. (φ from) 24 h |
|---|---|---|
| Dicyclohexylamine | 94.2 | 92.7 |
| Cyclohexylamine | 3.7 | 2.8 |
| N-Cyclohexylaniline | — | 2.8 |
| Cyclohexanol | 1.9 | 1.7 |

EXAMPLE 8

400 g of bead-shaped $\gamma$-$Al_2O_3$ with a diameter of 2-5 mm and a specific surface of 350 m²/g were impregnated with a solution of 23.3 g of $NbCl_5$ in 120 g of 37% strength hydrochloric acid, and thereafter dried at 120° C. Thereafter the catalyst support was impregnated with 410 g of a 16.9% strength by weight aqueous solution of ammonia, and subsequent washed free of chloride with water and dried again. 150 g of the so produced catalyst support were impregnated with a solution which had been prepared from 3.13 g Pd acetate and 40 g of acetonitrile. After again drying at 120° C. the catalyst was ready for use.

With 60 ml (53 g) of the so produced catalyst the hydrogenation of aniline was carried out. For that purpose the catalyst was brought into an upright standing pressure tube (internal diameter = 14 mm, length ca. 70 cm). The catalyst was first activated with hydrogen during 3 hours at 250° C. and 276 bar, 60 l of hydrogen hourly being released at the lower end of the pressure tube.

The temperature was then lowered to 200° C., and at 275 bar aniline and hydrogen were passed into the catalyst from above. The liquid trickled downwards through the catalyst to a separator. 60 to 100 liters per hour of hydrogen were released at the top of the separator. The throughput of aniline corresponded to a catalyst loading in the range of 0.2 to 0.3 g of aniline/ml catalyst/h. The hydrogenation product was taken from the separator in regular intervals and analysed. The following product composition resulted depending on the hours of operation at a reaction temperature of 200° C. (the remainder to 100% is by-products):

| Time h | Aniline % | DCHA* % | CHA* % |
|---|---|---|---|
| 89 | 0.2 | 76.1 | 22.9 |
| 137 | — | 79.2 | 20.5 |
| 212 | — | 78.2 | 21.4 |
| 255 | — | 80.6 | 18.7 |
| 326 | 0.1 | 74.3 | 24.6 |
| 374 | — | 77.1 | 22.6 |

*DCHA = dicyclohexylamine;
CHA = cyclohexylamine

EXAMPLE 9

400 g of $\gamma$-$Al_2O_3$ granulate of the same type as in Example 8 were impregnated with a solution of niobium chloride which had been prepared from 11.64 g of $NbCl_5$, 11.64 g of NaCl and 100 g of water. This impregnation was repeated four times after a drying between the impregnations each at 120° C. Onto the dried catalyst support one had influenced for one hour 410 g of a 8.9% strength aqueous solution of ammonia; the support was then washed free of chloride with water and again dried. 100 g of the such prepared catalyst support were impregnated with a solution which has been prepared from 4.16 g of Pd acetate and 31 g of methylene chloride. After drying again, 60 ml (51.1 g) of the catalyst were employed for the hydrogenation of aniline in the same manner as in Example 8.

At 200° C. and 275 bar 368 g of aniline were passed through the catalyst in 21 hour. 220 l of hydrogen were released hourly at the top of the product separator. The gaschromatographic analysis resulted in 23% cyclohexylamine and 76.9% dicyclohexylamine.

EXAMPLE 10

4 g of $TaCl_5$ were dissolved in 6.8 g of 37% strength hydrochloric acid and then diluted with 25 g of water. 100 g of $\gamma$-$Al_2O_3$ granulate (diameter=2–5 mm, specific surface=350 m$^2$/g) were impregnated with the thus prepared tantalum chloride solution. After drying at 100° C. under water jet vacuum the catalyst support was impregnated with 25 g of 19.3% strength aqueous solution of ammonia and then washed in fluent water until free of chloride. After a further drying, the catalyst support was impregnated with a solution which had been prepared from 4.16 g of Pd acetate and 35 g of methylene chloride. After subsequent drying the catalyst was ready for use. 60 ml (49.4 g) of the thus prepared catalyst were employed for the continuous hydrogenation of aniline according to Example 8. Under stationary conditions 935 g of aniline were passed through the catalyst in the course of 42 hours at 196° C. and a hydrogen pressure of 270 bar. 140 liters of hydrogen were released hourly from the product separator. The product collected in the separator contained 18.9% cyclohexylamine and 81% dicyclohexylamine.

What is claimed is:

1. A process for the preparation of a mixture of optionally substituted cyclohexylamine and optionally substituted dicyclohexylamine by catalytic hydrogenation of optionally substituted aniline on a supported noble metal catalyst, wherein a catalyst containing ruthenium, palladium or a mixture of both on a support containing niobic acid $Nb_2O_5.nH_2O$, tantalic acid $Ta_2O_5.nH_2O$ or a mixture of both, which contains the noble metal(s) in a total amount from 0.05 to 5% by weight and in the case of an Ru/Pd mixture, contains both metals in a weight ratio of 1:9–9:1, all percentages being based on the total weight of the catalyst is employed and the reaction is carried out at a temperature in the range from 100° to 340° C. and at a pressure of 100 to 500 bar.

2. The process of claim 1, wherein the reaction is carried out in the range of 130° to 240° C.

3. The process of claim 1, wherein the reaction is carried out at a pressure of 100 to 400 bar.

4. The process of claim 1, wherein the reaction is carried out continuously in the liquid phase on a fixed catalyst packing and a catalyst loading of 0.05–3 kg of optionally substituted aniline per liter of catalyst and per hour is set.

5. The process of claim 4, wherein a catalyst loading of 0.1–2 kg of optionally substituted aniline per liter of catalyst and per hour is set.

6. The process of claim 1, wherein an aniline of the formula

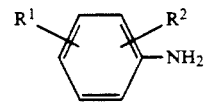

is employed in which
R$^1$ and R$^2$ independently of one another denote hydrogen, $C_1$–$C_4$-alkyl or $C_1$–$C_4$-alkoxy.

7. The process of claim 1, wherein, as the substituted aniline, the cyclohexylideneaniline of the formula

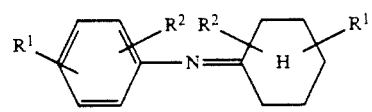

is employed, in which
R$^1$ and R$^2$ independently of one another denote hydrogen, $C_1$–$C_4$-alkyl or $C_1$–$C_4$-alkoxy.

8. The process of claim 7, wherein the cyclohexylideneaniline is employed in the form of a mixture of the underlying, optionally substituted cyclohexanone with the underlying, optionally substituted aniline.

9. The process of claim 3, wherein the reaction is carried out in the range of 130° to 240° C., the catalyst consists essentially of palladium on said support, the reaction is carried out continuously in the liquid phase on a fixed catalyst packing and a catalyst loading of 0.1–2 kg of optionally substituted aniline per liter of catalyst and per hour, and the aniline subjected to hydrogenation is of the formula

in which
R$^1$ and R$^2$ independently of one another denote hydrogen, $C_1$–$C_4$-alkyl or $C_1$–$C_4$-alkoxy.

* * * * *